(12) United States Patent
Sweitzer

(10) Patent No.: US 10,959,738 B2
(45) Date of Patent: Mar. 30, 2021

(54) OSTEOTOME

(71) Applicant: Shukla Medical, St. Petersburg, FL (US)

(72) Inventor: Zachary Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 0 days.

(21) Appl. No.: 16/325,328

(22) PCT Filed: Aug. 30, 2017

(86) PCT No.: PCT/US2017/049492
§ 371 (c)(1),
(2) Date: Feb. 13, 2019

(87) PCT Pub. No.: WO2018/045105
PCT Pub. Date: Mar. 8, 2018

(65) Prior Publication Data
US 2019/0201008 A1    Jul. 4, 2019

Related U.S. Application Data

(60) Provisional application No. 62/381,381, filed on Aug. 30, 2016.

(51) Int. Cl.
*A61B 17/16* (2006.01)
*A61B 17/92* (2006.01)
*A61F 2/46* (2006.01)

(52) U.S. Cl.
CPC .......... *A61B 17/1604* (2013.01); *A61B 17/92* (2013.01); *A61B 2017/922* (2013.01); *A61F 2002/4619* (2013.01)

(58) Field of Classification Search
CPC ....................................................... A61B 17/16
See application file for complete search history.

(56) References Cited

U.S. PATENT DOCUMENTS

| D193,556 S | 9/1962 | Lebourg et al. |
| 4,150,675 A | 4/1979 | Comparetto |
| D337,160 S | 7/1993 | Evans |
| 5,237,985 A * | 8/1993 | Hodgson ................ A61N 1/321 600/202 |
| 5,261,922 A | 11/1993 | Hood |

(Continued)

FOREIGN PATENT DOCUMENTS

| JP | 2005246036 A | 9/2005 |
| JP | 2013511351 A | 4/2013 |
| JP | 20130527718 A | 6/2013 |

OTHER PUBLICATIONS

International Search Report dated Nov. 27, 2017 in international application No. PCT/US2017/049492.

(Continued)

*Primary Examiner* — Christopher J Beccia
(74) *Attorney, Agent, or Firm* — Kim IP Law Group LLC

(57) ABSTRACT

An osteotome is provided that is designed for implanting and extracting medical device implants. The osteotome includes a handle, a blade attachment assembly about a first end of the handle for receiving a blade, and a wing assembly about a second end of the handle opposite the first end. The wing assembly further includes a wing extending outwardly from the handle.

19 Claims, 18 Drawing Sheets

(56) References Cited

U.S. PATENT DOCUMENTS

| | | |
|---|---|---|
| D385,164 S | 10/1997 | Hutchins et al. |
| 5,683,406 A | 11/1997 | Altobelli et al. |
| 5,997,298 A | 12/1999 | Nowak |
| D466,213 S | 11/2002 | Snitkin et al. |
| D503,800 S | 4/2005 | Ebner |
| D536,791 S | 2/2007 | Eskridge et al. |
| D554,256 S | 10/2007 | Eskridge et al. |
| D562,981 S | 2/2008 | Trissel et al. |
| D601,869 S | 10/2009 | Nelson |
| D603,231 S | 11/2009 | Fisher et al. |
| 7,704,254 B2 | 4/2010 | Walen |
| D631,154 S | 1/2011 | Hamilton, Jr. |
| D699,342 S | 2/2014 | Suzuki |
| D699,348 S | 2/2014 | Morejon |
| 8,740,912 B2 | 6/2014 | Stark |
| D742,002 S | 10/2015 | Fisher et al. |
| D745,349 S | 12/2015 | Hampton et al. |
| D745,350 S | 12/2015 | Hampton et al. |
| D778,443 S | 2/2017 | Brannon |
| D793,556 S | 8/2017 | Sweitzer |
| D802,763 S | 11/2017 | Sweitzer |
| 2001/0037114 A1 | 11/2001 | Dinger et al. |
| 2005/0049623 A1 | 3/2005 | Moore et al. |
| 2009/0306669 A1 | 12/2009 | Takahashi |
| 2010/0121331 A1 | 5/2010 | Sharp et al. |
| 2010/0249785 A1* | 9/2010 | Betts ............ A61B 17/1617 606/79 |
| 2010/0331851 A1 | 12/2010 | Huene |
| 2012/0049973 A1 | 3/2012 | Smith et al. |
| 2013/0096680 A1 | 4/2013 | Ribeiro et al. |
| 2013/0261630 A1 | 10/2013 | Courtney et al. |
| 2016/0128716 A1 | 5/2016 | Cao et al. |
| 2017/0000509 A1 | 1/2017 | Kato et al. |
| 2017/0100134 A1 | 4/2017 | Gibson |
| 2017/0120021 A1 | 5/2017 | Krastev |

OTHER PUBLICATIONS

Written Opinion dated Nov. 27, 2017 in international application No. PCT/US2017/049492.

Examination Report for Australian Patent Application No. 2017318574 dated Mar. 22, 2019.

Translation of Office Action for Japanese Patent Application No. 2019-512712 dated Nov. 14, 2019.

* cited by examiner

OSTEOTOME

CROSS-REFERENCE TO RELATED APPLICATIONS

This application is a U.S. national phase application under 35 U.S.C. § 371 of International Patent Application No. PCT/US2017/049492 filed Aug. 30, 2017, which claims the benefit of U.S. Provisional Application No. 62/381,381 filed Aug. 30, 2016, the entire disclosures of which are incorporated by reference herein in their entirety.

BACKGROUND OF THE INVENTION

The exemplary embodiments of the subject disclosure relate generally to the field of medical device implant extraction tools. In particular, the subject disclosure relates to an osteotome having a quick releasable blade and a wing assembly.

During implant extraction, medical device implant extraction tools such as osteotomes are utilized to remove or extract an implant from bone. The osteotome can be used to cut a bone surface to shape it or remove bone for purposes of extracting a medical implant from the bone.

Conventional osteotomes are limited in their functionality due to particular design, which consequently reduces their effectiveness for facilitating implant extraction. Therefore, there is still a need for a more efficient and economical osteotome to better assist medical device implant extraction procedures.

BRIEF SUMMARY

In accordance with an exemplary embodiment of the subject disclosure, there is provided an osteotome comprising a handle, a blade attachment assembly about a first end of the handle for receiving a blade, and a wing assembly about a second end of the handle opposite the first end. The wing assembly includes a wing extending outwardly from the handle.

In an aspect of the exemplary embodiment, the wing assembly is pivotably mounted to the handle. The wing assembly also includes a housing and the wing is pivotably mounted to the housing. The wing assembly is also releasably attached to the housing. The housing includes a recess for receiving the wing in the housing. The wing assembly further includes a locking mechanism to releasably lock the wing in a fixed position relative to a longitudinal axis of the handle. The locking mechanism includes a detent extending from the wing and a plurality of corresponding detents about the housing. The detent is a tab and the plurality of corresponding detents are chamfered edges circumferentially positioned about the housing.

In another aspect of the exemplary embodiment, the wing extends perpendicular to a longitudinal axis of the handle and is rotatably secured to a proximal end of the handle. The wing includes a boss member pivotably attached to the handle. The boss member is concentric with the handle. The boss member includes a locking groove for securing the wing to the housing. The locking groove is an annular groove.

In yet another aspect of the exemplary embodiment, the blade attachment assembly includes a housing for receiving a blade and a locking mechanism for releasably securing the blade to the housing. The housing includes a recess for receiving the blade. The locking mechanism includes a pair of detents for engaging a pair of notches on the blade. The locking mechanism moves between a locked position and an unlocked position for releasably securing the blade. The osteotome further includes a biasing member that biases the locking mechanism toward the locked position. The biasing member is a spring.

In another aspect of the exemplary embodiment, the osteotome further includes a blade releasably secured to the blade attachment assembly. The blade includes a pair of notches for aligning the blade with the handle. The blade also includes a plurality of indicators along a length of the blade. The blade further includes a beveled edge.

In accordance with another aspect of the exemplary embodiment, the wing includes a base, an extension member extending from the base, and an impact plate extending from the extension member. The extension member extends parallel to a longitudinal axis of the handle. The impact plate extends radially outwardly from a longitudinal axis of the handle. The wing further includes a guard pivotably attached to the extension member. The guard is movable between a first position and a second position. The osteotome further includes a locking member for securing the guard in a fixed position.

Other features and advantages of the subject disclosure will be apparent from the following more detailed description of the exemplary embodiments, taken in conjunction with the accompanying drawings which illustrate, by way of example, the principles of the subject disclosure.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the subject disclosure, there are shown in the drawings exemplary embodiments. It should be understood, however, that the invention is not limited to the precise arrangements and instrumentalities shown.

In the drawings.

DETAILED DESCRIPTION OF THE INVENTION

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any matter not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the subject disclosure can be presented in a range format. It should be understood that the description in range format is merely for convenience and brevity and should not be construed as an inflexible limitation on the scope of the exemplary embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the exemplary embodiments can be practiced without one or more of the specific features or advantages of a particular embodiment. In other instances, additional features and advantages may be recognized in certain embodiments that may not be present in all exemplary embodiments of the subject disclosure.

Figure 1:
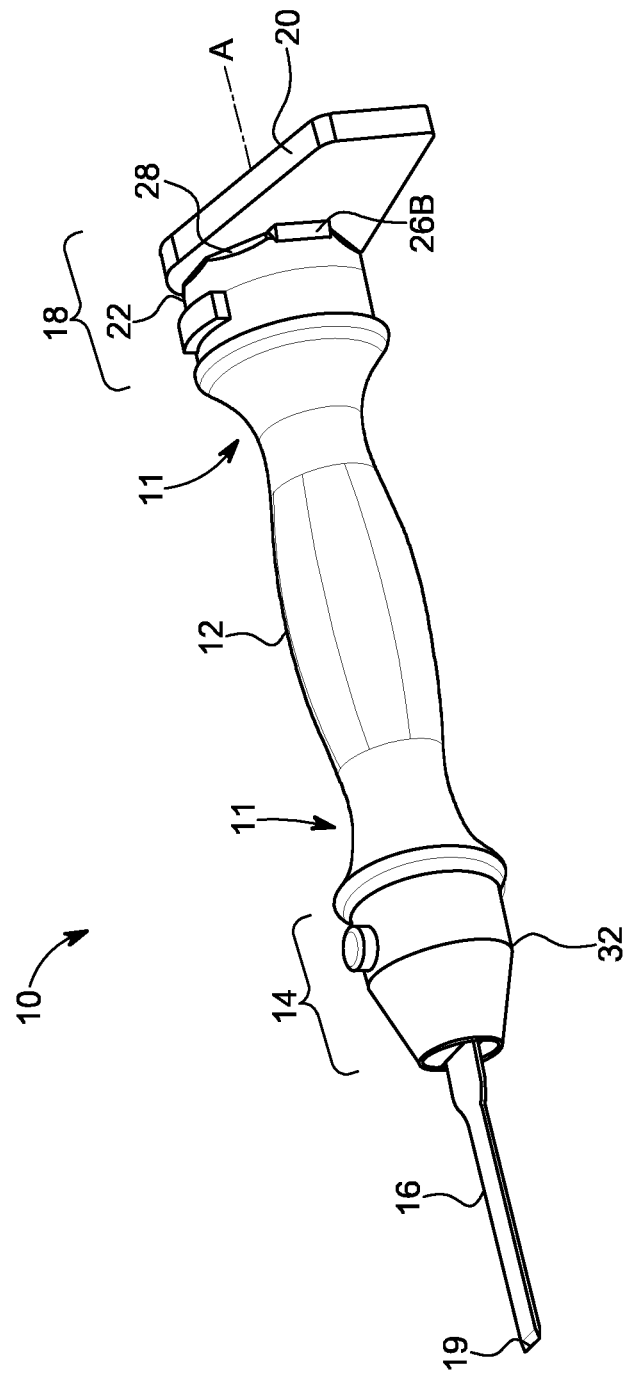
FIG. 1 is a perspective view of an osteotome in accordance with an exemplary embodiment of the subject disclosure.
Figure 2:
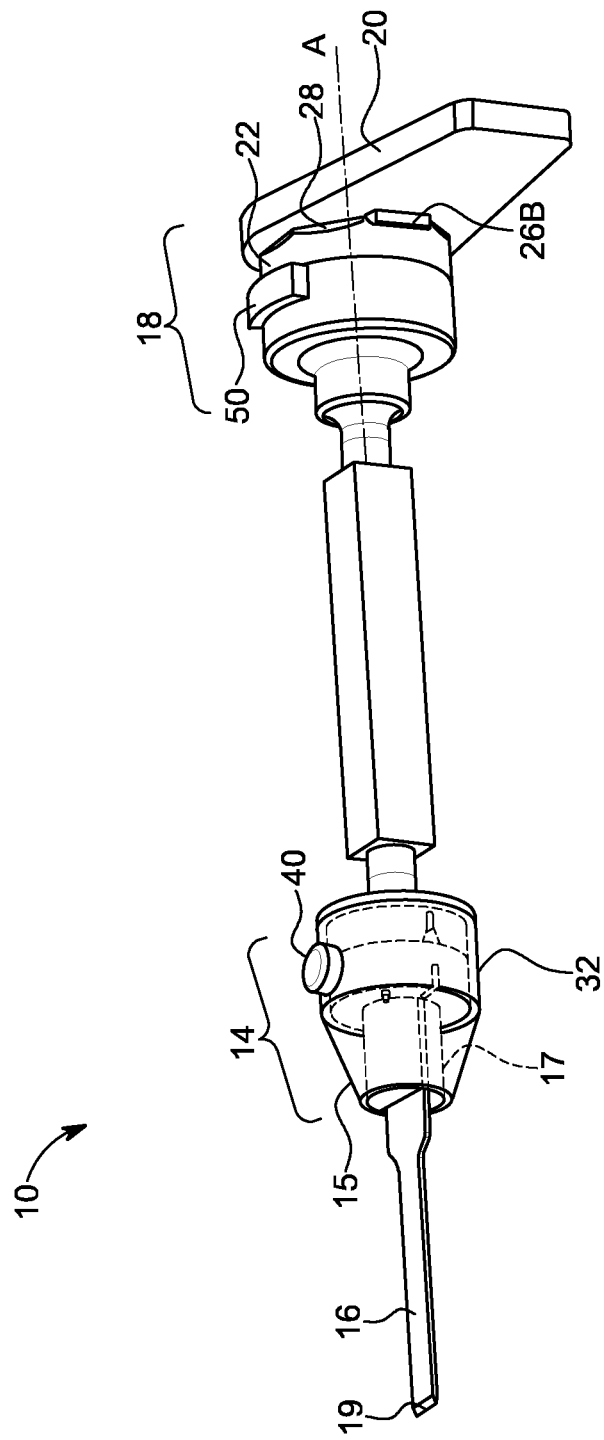
FIG. 2 is a perspective view of the osteotome of FIG. 1 with certain parts omitted.
Figure 3:
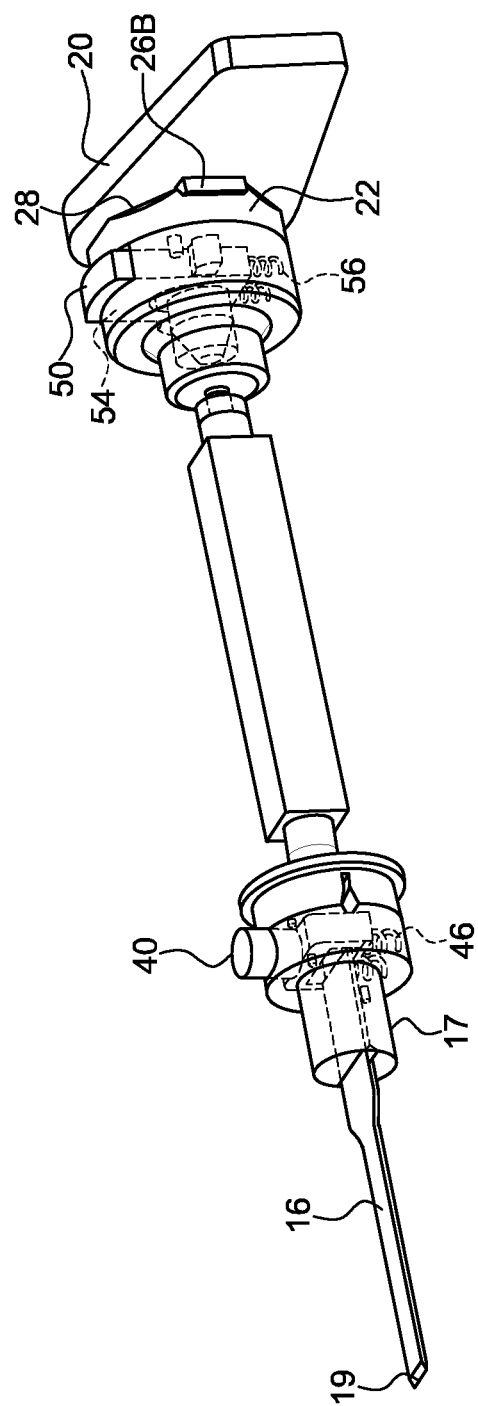
FIG. 3 is another perspective view of the osteotome of FIG. 1 with certain parts omitted.
Figure 4:
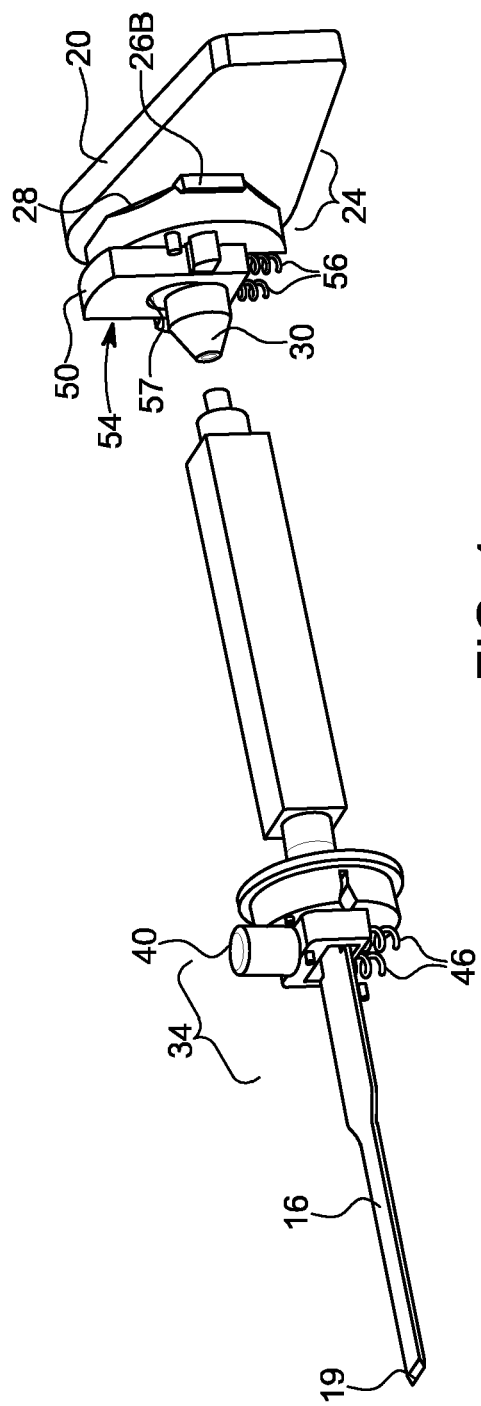
FIG. 4 is another perspective view of the osteotome of FIG. 1 with certain parts omitted.

Referring now to the drawings wherein aspects of the subject disclosure are shown, FIGS. 1-18 illustrate an osteotome 10 in accordance with an exemplary embodiment. The osteotome 10 includes a handle 12, a blade attachment assembly 14 about a first end of the handle for receiving a blade 16, and a wing assembly 18 about a second end of the handle opposite the first end. The wing assembly 18 includes a wing 20 extending outwardly from the handle 12. FIG. 1 shows the wing extending radially outwardly from the handle.

The handle 12 is generally an elongated member that is preferably rigid and sized sufficiently to be gripped by a hand of a user. As best shown in FIG. 1, the handle 12 is generally a substantially cylindrical member having a longitudinal central axis and a substantially circular cross-section. However, the handle 12 can have any cross-sectional shape such as hexagonal, polygonal or any other cross-sectional shape suitable for its intended purpose. The handle 12 can also be formed with a plurality of handle segments having different cross-sectional diameters.

Generally, the handle 12 is illustrated as straight, although it may have a lordotic curve or be otherwise bent or curved. The handle 12 may have any desired length sufficient for its intended purpose.

The handle includes gripping portions 11 that aid a user's ability to grip and move the osteotome. As best shown in FIG. 1, the gripping portion 11 may be located adjacent the first end (a distal end) of the handle 12 or the second end (a proximal end) of the handle. The gripping portion 11 may be configured as any suitable shape that may aid a user's ability to grip the osteotome such as finger slots, depressions, grooves or a textured surface.

Figure 5:
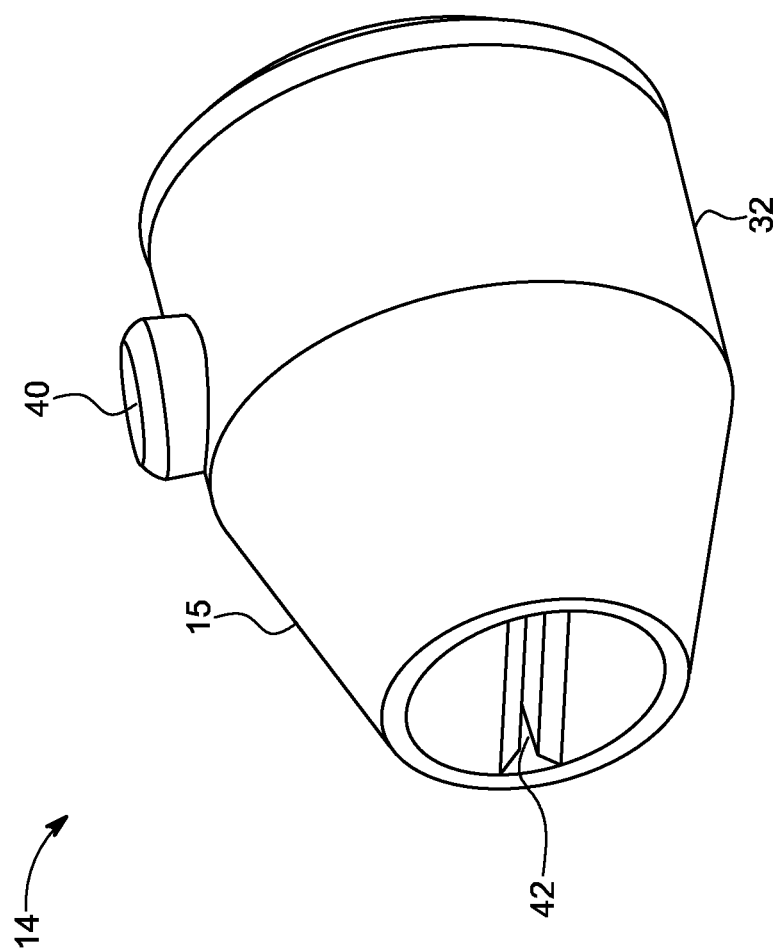
FIG. 5 is a front perspective view of a blade attachment assembly of the osteotome of FIG. 1.
Figure 6:
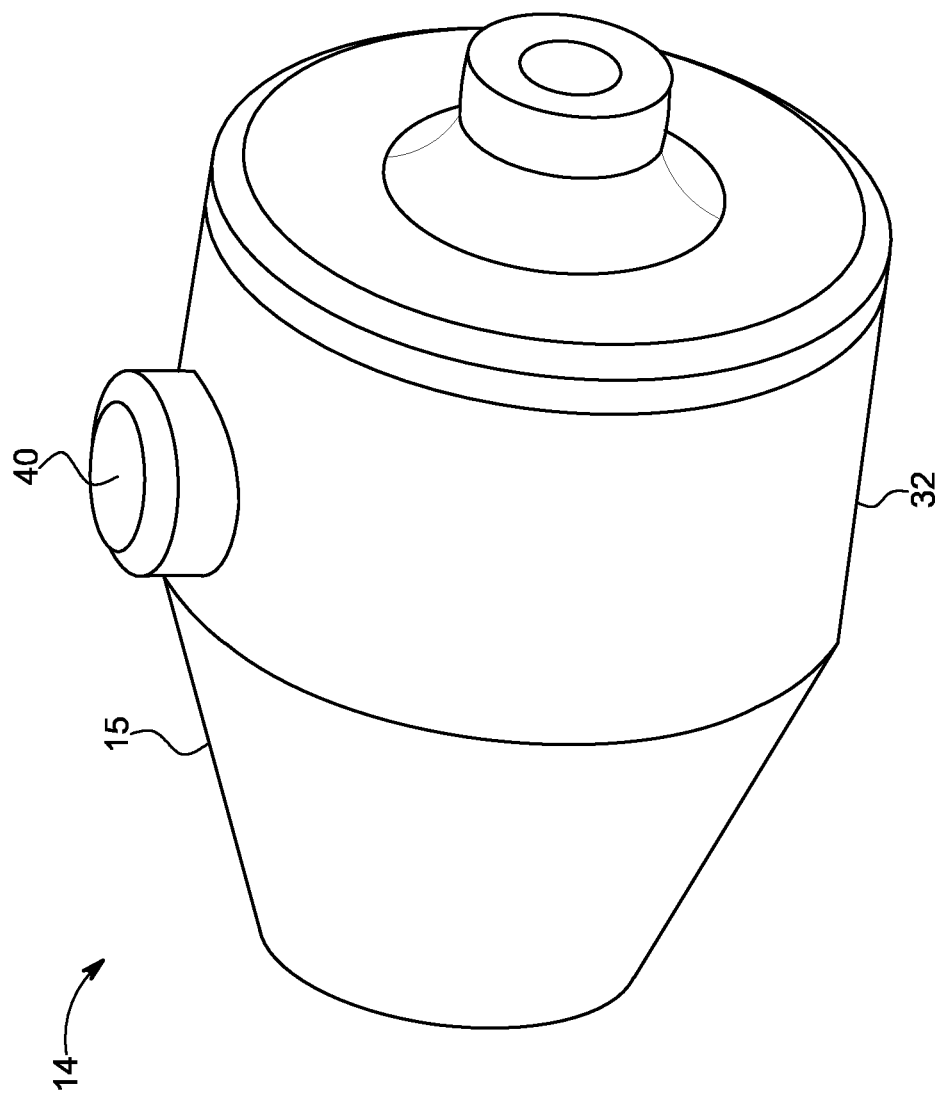
FIG. 6 is a rear perspective view of the blade attachment assembly of FIG. 5.

Referring to FIGS. 2-6, 12 and 14-16, the blade attachment assembly 14 includes a mount i.e., a housing 32 for receiving the blade 16 and a locking mechanism 34 for releasably securing the blade 16 to the blade attachment assembly. The housing 32 includes a recess i.e., a slot 42 for receiving the blade 16 in the housing. Preferably, the slot 42 is configured as a rectangular shaped slot corresponding to a shape and size of the blade 16. However, the slot 42 may be any shape suitable for its intended purpose of receiving the blade and aiding in rigidly supporting the blade. In an aspect, the housing 32 includes a nose 17 adjacent the locking mechanism 34 for receiving the blade there through. FIGS. 5 and 6 illustrate the configuration of the housing 32 of the blade attachment assembly 14.

Figure 12:
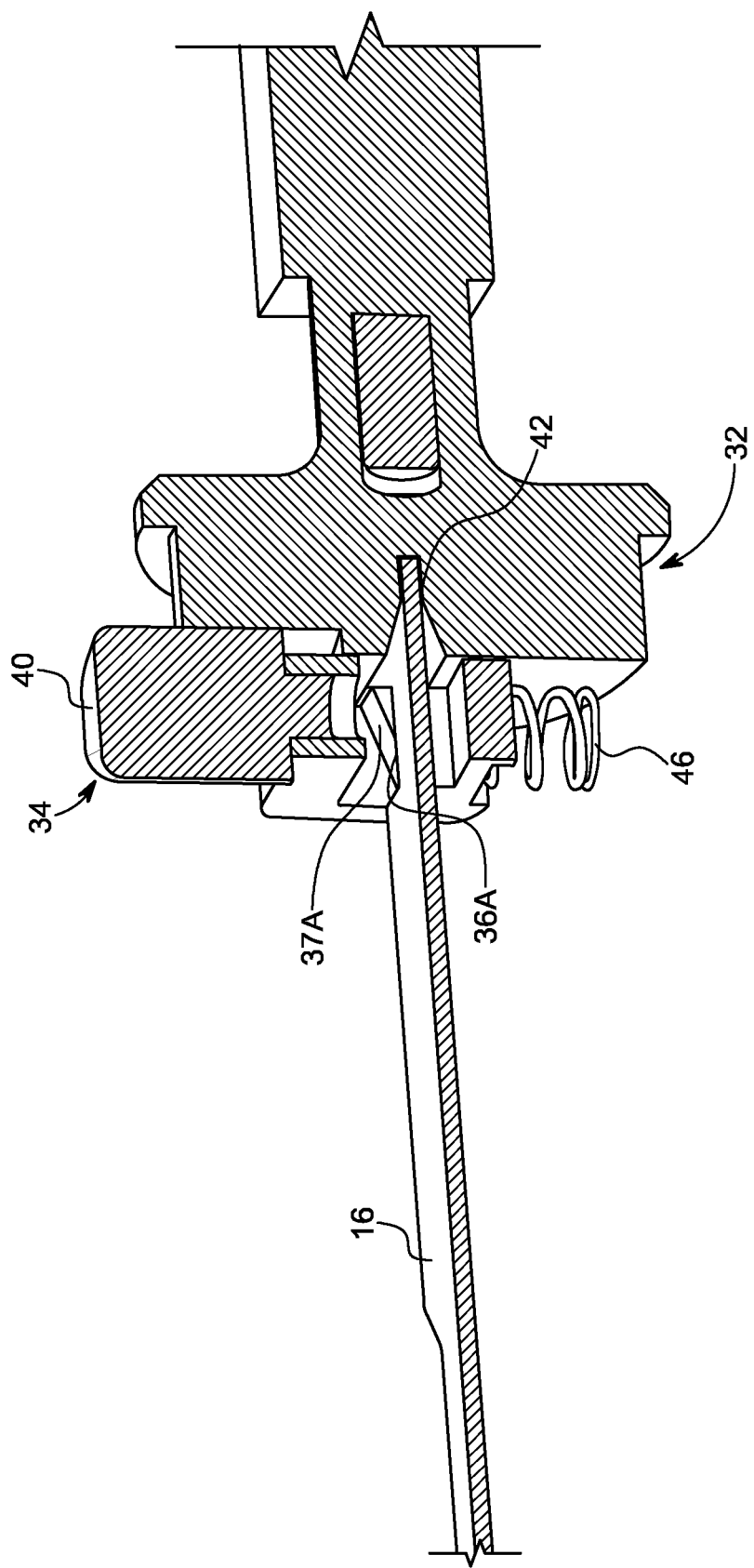
FIG. 12 is a partial cross-sectional perspective view of a blade attachment assembly of the osteotome of FIG. 1.
Figure 14:
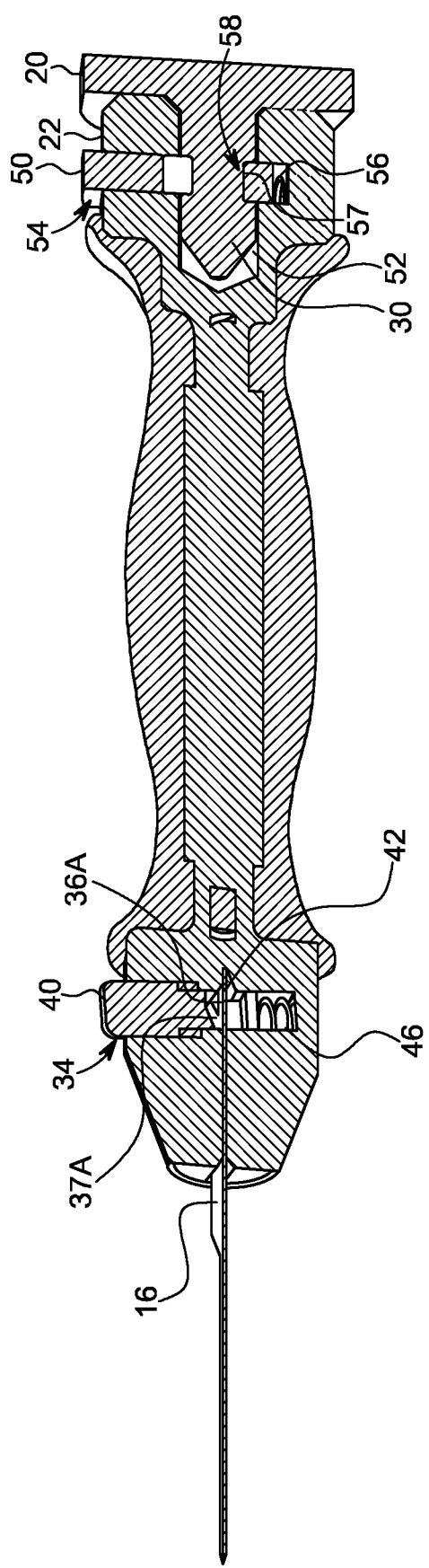
FIG. 14 is a cross-sectional perspective view of the osteotome of FIG. 1.
Figure 15:
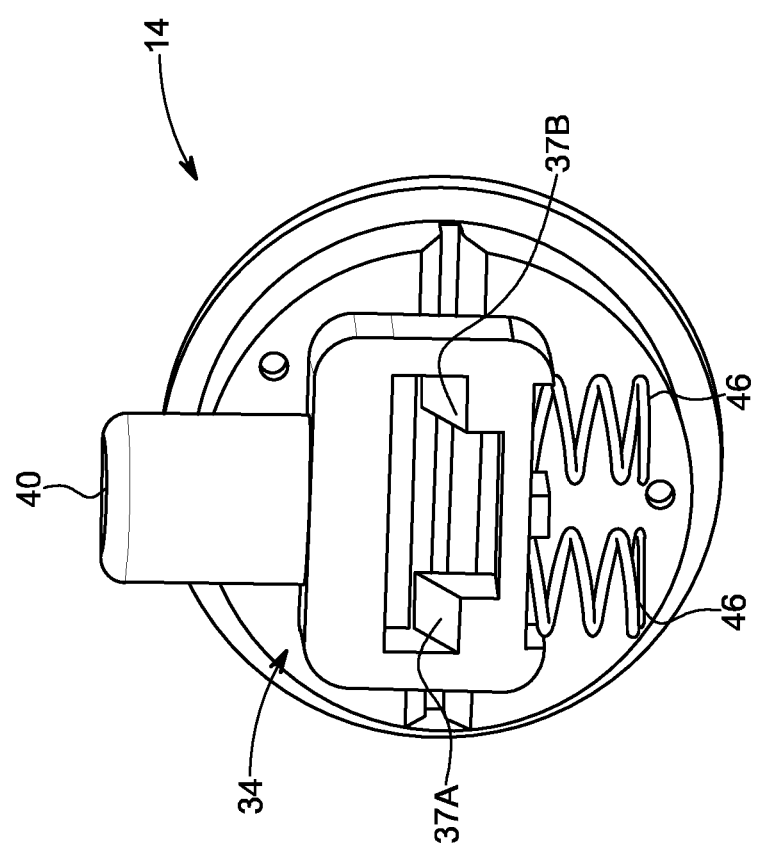
FIG. 15 is a partial front perspective view of a blade attachment assembly of the osteotome of FIG. 1 with certain parts omitted.
Figure 16:
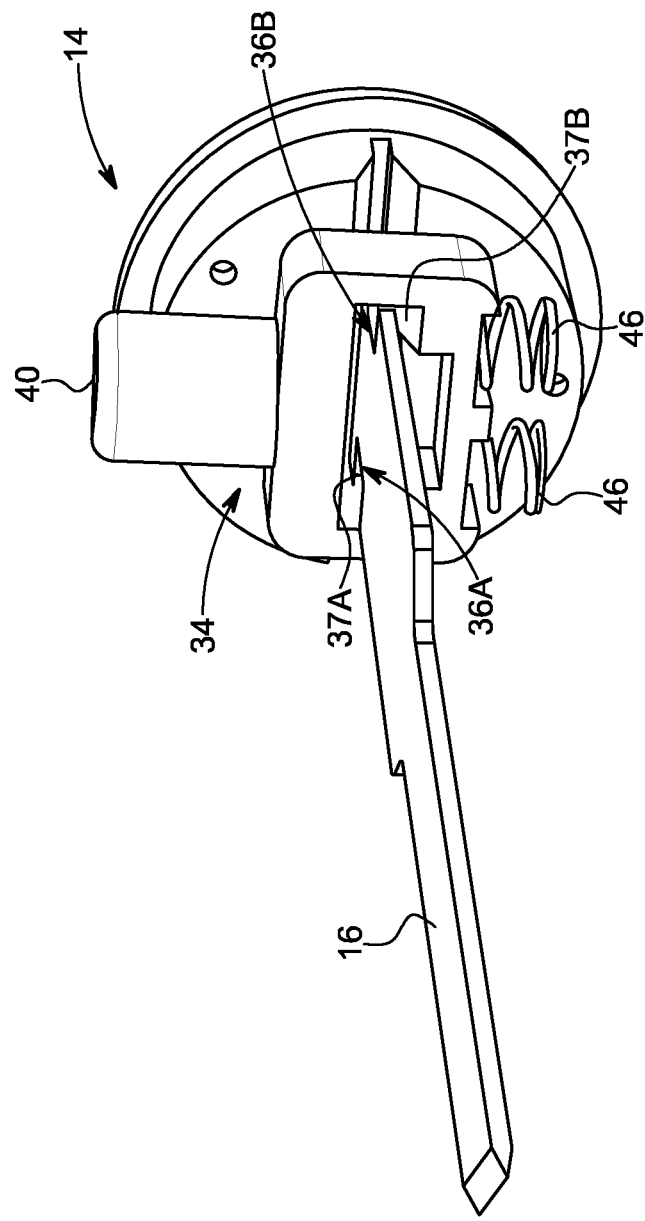
FIG. 16 is another partial front perspective view of a blade attachment assembly of the osteotome of FIG. 1 with certain parts omitted.

FIGS. 12 and 14 show a cross-section of the locking mechanism 34 for releasably securing the blade 16 to the blade attachment assembly 14. The locking mechanism 34 includes a quick release button 40 positioned about a dorsal end of the locking mechanism 34 for loading the blade 16 into the osteotome 10. As shown in FIGS. 15 and 16, the locking mechanism 34 also includes a pair of sloped detents or locking tabs 37A, 37B spaced apart for engaging a pair of respective notches on the blade 16. The pair of sloped detents can be integrally formed with the quick release button, or alternatively rigidly connected thereto. As shown in FIG. 16, the locking tabs 37A, 37B are of unitary construction such that they move uniformly.

In accordance with an aspect of the exemplary embodiment, the blade attachment assembly 14 includes a sleeve 15 that is affixed to and surrounds the housing 32 and the locking mechanism 34. The sleeve 15 provides a confining force that allows the housing 32 and the locking mechanism 34 to lie in a substantially parallel entrusted relationship for securing the blade 16 to the blade attachment assembly 14. The housing 32 and sleeve 15 include an aperture allowing passage of the quick release button 40 there through.

In accordance with an exemplary embodiment, a biasing member 46 continuously biases the locking mechanism 34 toward a locking position (as shown in FIG. 12). As configured and shown in FIGS. 3, 4, 12 and 14-16, the biasing member 46 is disposed below and adjacent each of the locking tabs 37A, 37B of the locking mechanism 34. Specifically, the biasing member 46 is secured in position against the underside of the locking tabs 37A, 37B. The biasing member 46 is preferably configured as a coil spring. However, the biasing member can alternatively be an elastomeric member, clock spring or any other biasing member suitable for the intended purpose.

The locking mechanism 34 moves between a locked or locking position (FIG. 12) and an unlocked position (FIG. 16) for releasably securing the blade. Upon depression of the quick release button 40, a user applies a force to the locking mechanism 34 in a direction transverse to a longitudinal axis of the blade 16 to bias the locking mechanism 34 toward the unlocked position. In the unlocked position, the blade 16 is free to move in and out of the slot 42 of the housing 32. Upon release of the button 40, the locking mechanism 34 is biased to the locked position by the biasing member 46. The pair of sloped detents or locking tabs 37A, 37B are sloped in the anterior direction so as to assist in the passage of the blade past its posterior ends.

Figure 7:
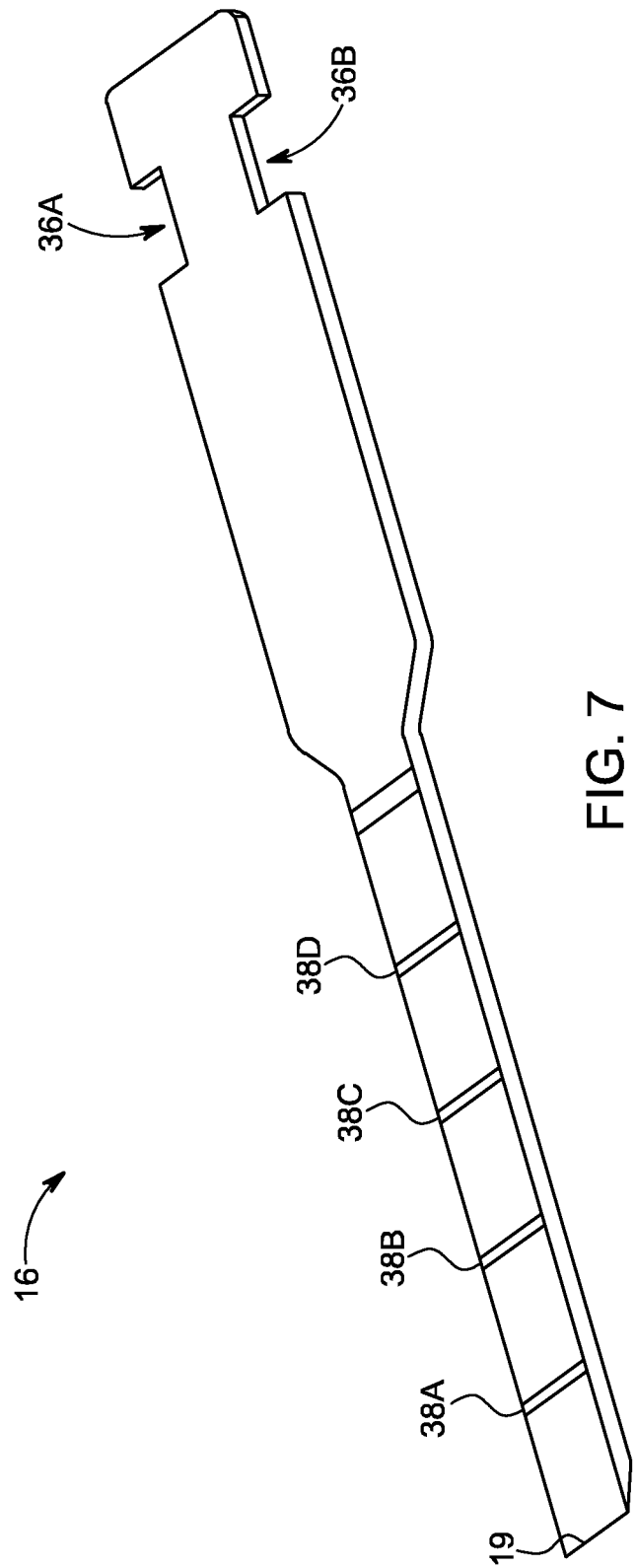
FIG. 7 is a perspective view of a blade of the osteotome of FIG. 1.

FIG. 7 shows a perspective view of the blade 16 applicable to the osteotome 10 of the subject disclosure. In an aspect, the blade is releasably secured to a distal end of the handle. The osteotome 10 is configured to receive a variety of blades having variable lengths. The blade 16 can be sized and shaped with any thickness or width suitable for being received within the slot 42. Preferably, the blade 16 includes a beveled edge 19.

In accordance with an exemplary embodiment, a proximal end of the blade 16 includes a pair of notches 36A, 36B for securing the blade 16 to the blade attachment assembly 14 (FIG. 7). Specifically, the notches 36A, 36B lock the blade in position via the locking mechanism 34 when the blade is attached to the osteotome 10. The notches 36A, 36B also facilitate aligning the blade with the handle.

In use, the locking tabs 37A, 37B of the locking mechanism 34 are each operatively engaged with the pair of notches 36A, 36B respectively, for releasably securing the blade. As the locking tabs 37A, 37B are biased to the locked position by the biasing member 46, the locking tabs engage the respective notches 36A, 36B on the blade. In the locked position (FIG. 12), the locking tabs 37A, 37B are configured to engage respective notches 36A, 36B for securing the blade 16 in position.

In an aspect of the exemplary embodiment illustrated in FIG. 7, the blade 16 includes a plurality of indicators 38A-D along a length of the blade 16 for providing a visual indicator useful in indicating a depth of the blade 16 used in a procedure.

In accordance with an exemplary embodiment illustrated in FIGS. 1-4, the wing assembly 18 includes a mount i.e., a housing 22 and the wing 20 is pivotably mounted to the housing. The wing 20 is connected to the handle 12 about its second end opposite the blade attachment assembly 14. As shown in FIGS. 1-4 and 8, the wing 20 extends outwardly from the handle 12, and preferably radially outwardly from the housing 22. In an aspect, the wing assembly 18 is pivotably mounted to the handle.

Figure 9:
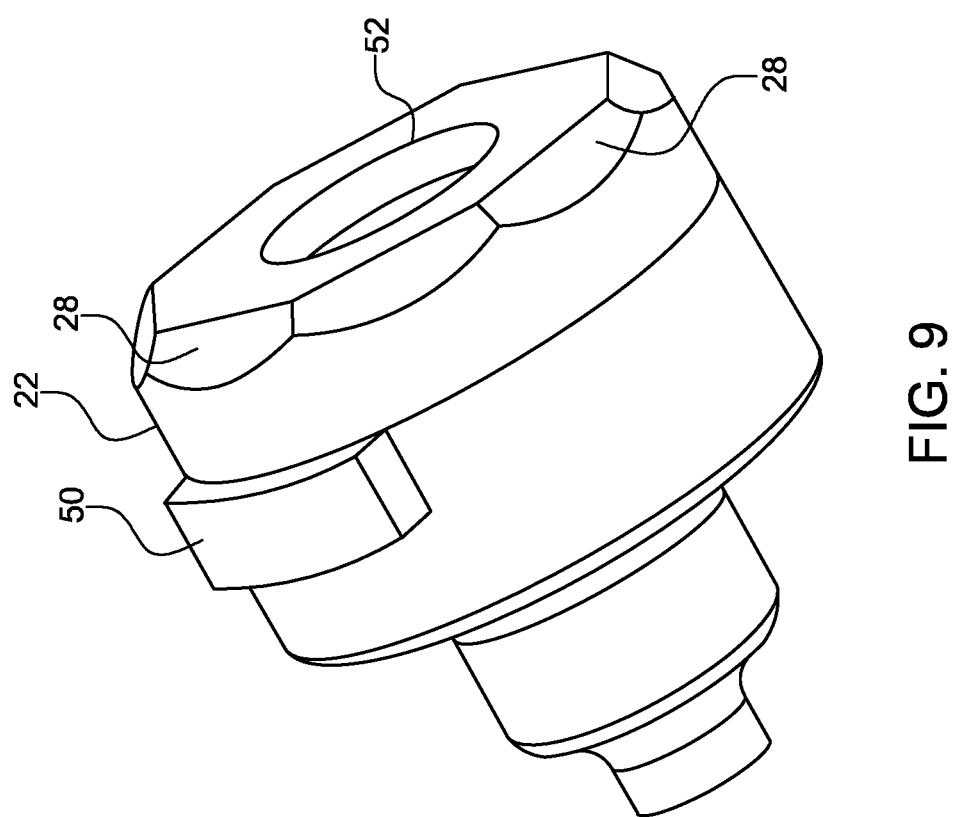
FIG. 9 is a perspective view of the wing assembly of FIG. 8 with certain parts omitted.
Figure 10:
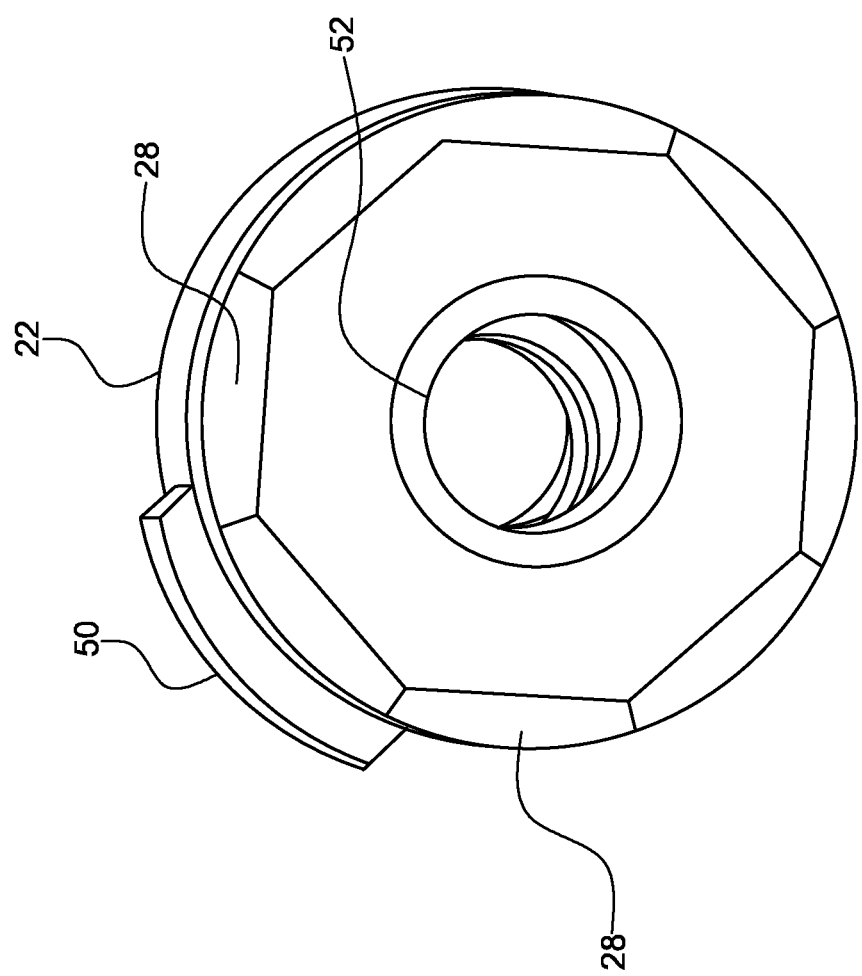
FIG. 10 is another perspective view of the wing assembly of FIG. 9.

Referring to FIGS. 4, 9, 10, 13 and 14, the housing 22 includes a recess i.e., an aperture 52 for receiving the wing 20 in the housing 22. Specifically, the aperture 52 is configured to receive a boss member 30 (FIG. 11) of the wing 20. The aperture 52 has a cross-sectional diameter larger than a cross-sectional diameter of the boss member 30. FIGS. 9 and 10 illustrate the configuration of the housing 22 of the wing assembly 18. The housing 22 includes a plurality of detents 28 circumferentially positioned about a periphery of the housing for adjustably securing the wing about a plurality of circumferential positions.

Figure 11:
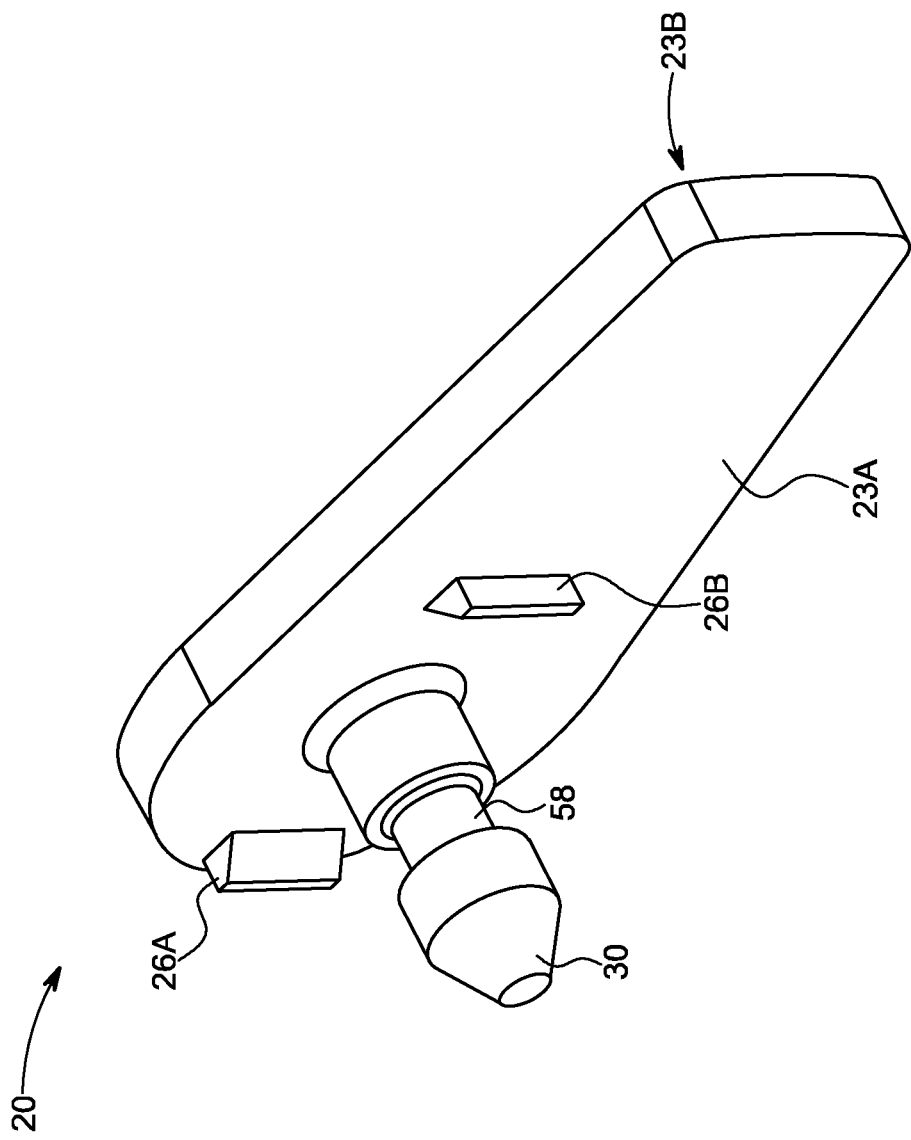
FIG. 11 is a perspective view of a wing of the wing assembly of FIG. 8.

In accordance with an exemplary embodiment, the wing is configured as shown in FIG. 11. The wing 20 is generally shaped as a planar member configured to receive an impact force from a surgical tool, such as a hammer. In use, an impact force on the wing 20 is transferred to the blade 16. For example, an impact force upon a bottom surface 23A of the wing 20 results in an upward force or a proximally directed force on the blade. Similarly, an impact force upon a top surface 23B of the wing 20 results in a downward or distally directed force on the blade, for example, for procedures involving cutting away portions of the bone.

Generally, the impact force can be applied to the bottom or top surfaces 23A, 23B of the wing 20 to drive the blade 16 of the osteotome 10 e.g., through bone or cement. The wing is configured as best shown in FIGS. 1-4, 8 and 11, but can alternatively be configured as any other shape suitable to receive and/or transfer forces acting on the wing 20 to the blade 16. In operation, the wing 20 is configured to receive an upward and downward force substantially parallel to a longitudinal axis of the osteotome 10.

Figure 8:
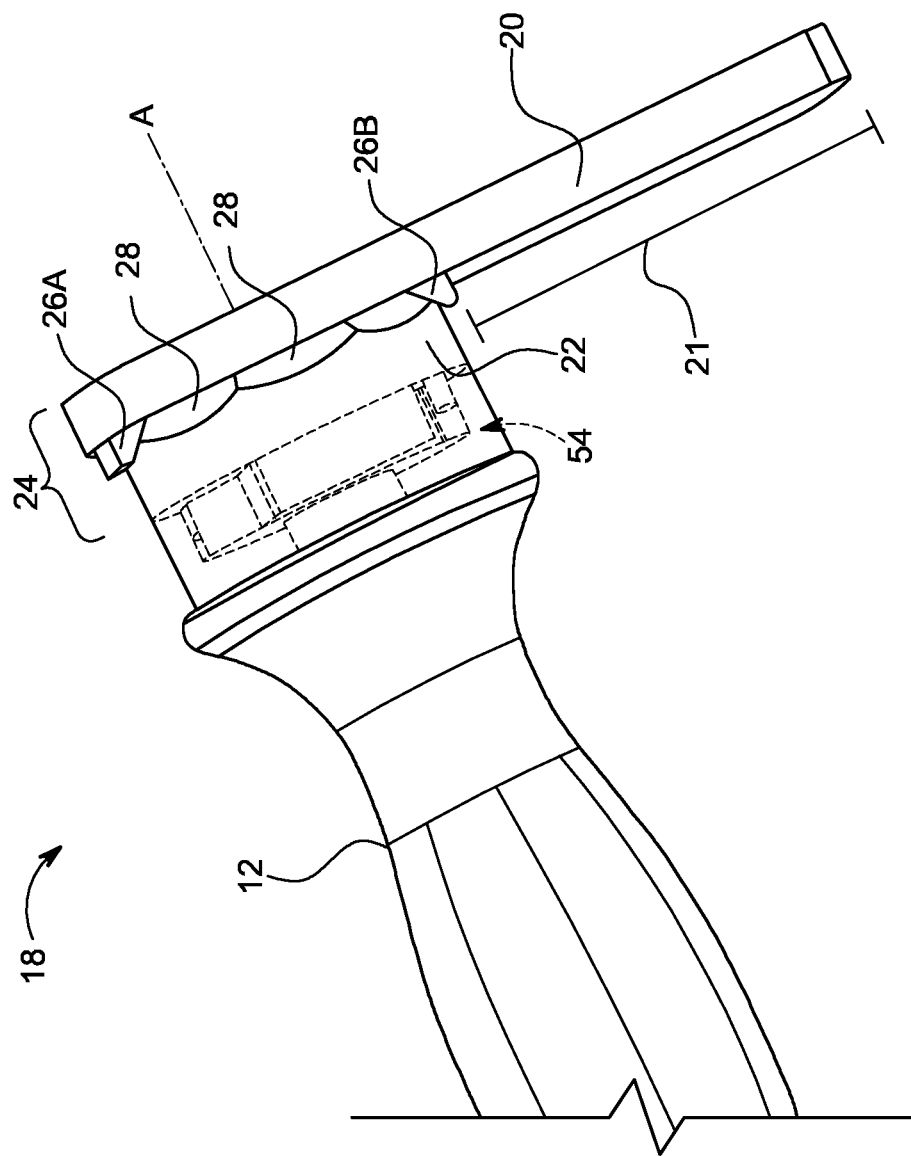
FIG. 8 is a partial top perspective view of a wing assembly of the osteotome of FIG. 1.

As shown, for example in FIG. 8, the wing 20 extends outwardly from the handle 12 and housing 22. Specifically, the wing 20 has an extension length 21 sized sufficiently to allow clearance between a surgical tool, e.g., a hammer, providing an upward or downward force on the wing 20 and a hand of a user on the handle 12 while avoiding interference with any adjacent soft tissue during a procedure. Preferably, the extension length 21 is about 1.5 inches to about 3.5 inches (but alternatively may be less than about 1.5 inches or greater than about 3.5 inches e.g., +/-0.1, 0.2, 0.3, 0.4, 0.5, 1.0, 2.0, 3.0 inches).

The wing 20 further includes boss member 30 for pivotably attaching to the handle 12. The boss member 30 is preferably configured as a cylindrical shaft and includes a locking groove 58 positioned along a length of the cylindrical shaft for engaging a securing mechanism 54 to secure the wing 20 to the housing 22. In an aspect, the boss member 30 is concentric with the handle 12 and the locking groove 58 is preferably an annular groove.

Figure 13:
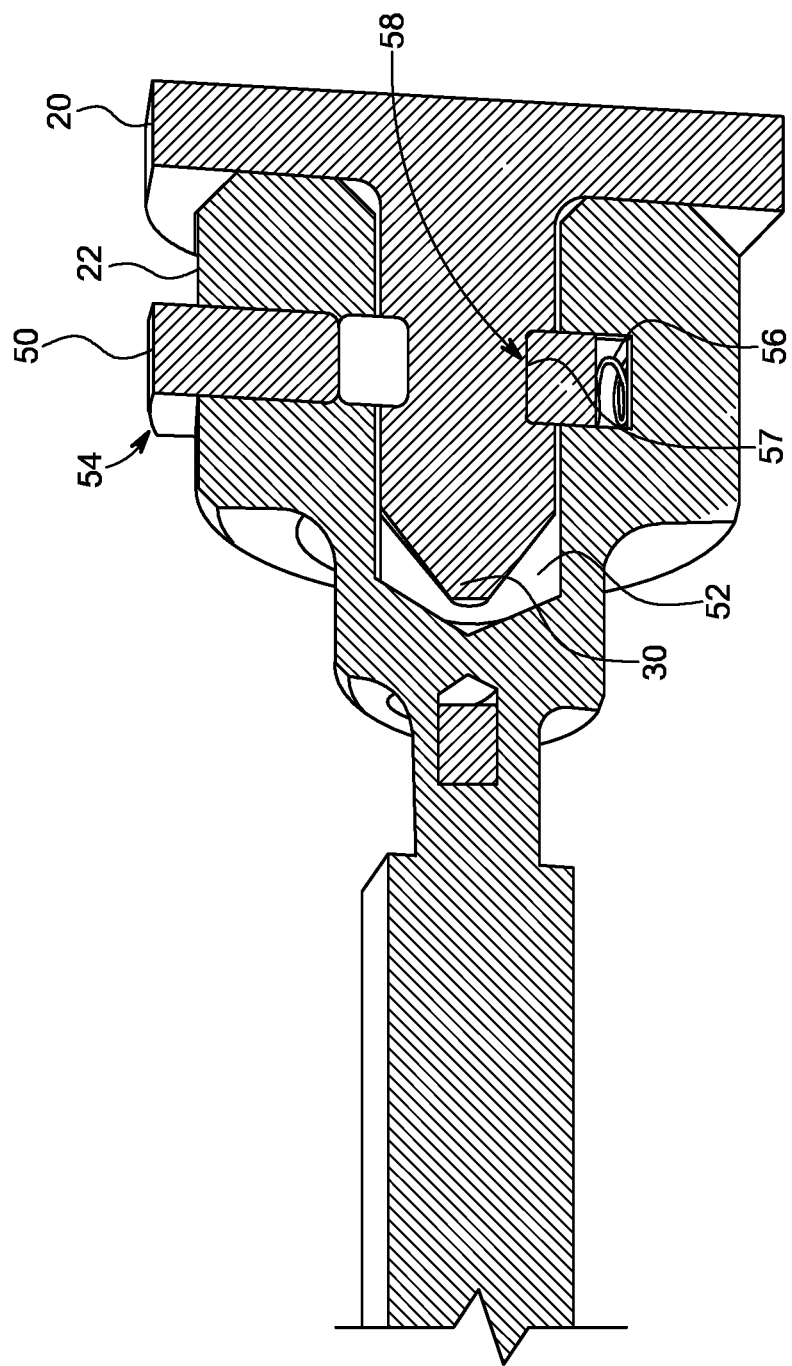
FIG. 13 is a partial cross-sectional perspective view of a wing assembly of the osteotome of FIG. 1.

Referring back to FIGS. 1, 13 and 14, the wing assembly 18 includes the securing mechanism 54 for releasably securing the wing 20 to the housing 22 such that the wing is releasably attached to the housing. FIGS. 13 and 14 show a cross-section of the securing mechanism 54 for releasably securing the wing 20 to the housing 22. The securing mechanism 54 includes a quick release button 50 positioned about a dorsal end of the securing mechanism 54 for securing the wing 20 to the osteotome 10. The securing mechanism 54 also includes a locking aperture 57 for engaging the annular locking groove 58 of the boss member 30. The locking aperture 57 can be integrally formed with the quick release button, or alternatively rigidly connected thereto.

A biasing member 56 continuously biases the securing mechanism 54 toward a locking position (as shown in FIG. 13). As configured and shown in FIGS. 3, 4, 13 and 14, the biasing member 56 is positioned adjacent a bottom portion of the securing mechanism 54. Specifically, the biasing member 56 is secured in position against the underside of the securing mechanism 54. The biasing member 56 is preferably configured as a coil spring. However, the biasing member can alternatively be an elastomeric member, clock spring or any other biasing member suitable for the intended purpose.

The securing mechanism 54 moves between a locked or locking position and an unlocked position. To release the wing, a user applies a force to depress the quick release button 50 in a direction transverse to a longitudinal axis of the boss member 30 to bias the securing mechanism 54 toward the unlocked position. In the unlocked position, the boss member 30 of the wing 20 is free to move in and out of the aperture 52 of the housing 22 and the locking aperture 57 of the securing mechanism 54. Upon release of the button 50, the securing mechanism 54 is biased to the locked position by the biasing member 56. Specifically, the locking aperture 57 engages the annular locking groove 58 of the boss member 30 such that the wing 20 is secured to the housing 22, but free to rotate about the housing.

Referring back to FIGS. 1-4 and 8, the wing assembly 18 further includes a locking mechanism 24 to releasably lock the wing 20 in a fixed position relative to a longitudinal axis A of the handle (FIG. 8). The locking mechanism 24 includes a detent and preferably a pair of detents 26A, 26B extending from the wing 20 (FIGS. 8 and 11) for engagement with the plurality of corresponding detents 28 about the housing 22 (FIGS. 9 and 10). Preferably, the detents 26A, 26B are configured as a pair of locking tabs, i.e., locking protrusions, and the plurality of corresponding detents 28 are configured as a plurality of chamfered edges circumferentially positioned about a periphery of the housing 22. The detents 26A, 26B are correspondingly chamfered, as best shown in FIG. 1, to mate with the chamfered edges of the corresponding detents 28.

As best shown in FIG. 8, the pair of detents 26A, 26B are configured to selectively engage the plurality of chamfered edges 28 when the locking mechanism 24 is in the locked position. Accordingly, the wing 20 is releasably secured in a fixed position relative to a longitudinal axis of the handle 12. In use, upon depression of the quick release button 50, the locking mechanism 24 moves to the unlocked position allowing the wing to rotate such that the opposing pair of locking tabs 26A, 26B disengage from corresponding chamfered edges 28. Advantageously, the wing 20 can be rotated when the blade 16 is immovable e.g., stuck within the bone of a patient.

Although the locking mechanism 24 is illustrated as having the pair of detents, i.e., locking tabs 26A, 26B, it is to be understood that the locking mechanism 24 can include additional locking tabs for engaging each of the plurality of chamfered edges 28. For example, in an aspect, the number of locking tabs and chamfered edges are equal. Various combinations with different amounts of locking tabs and chamfered edges could be utilized to increase or decrease the firmness of the fit between the locking tabs and chamfered edges when rotating the wing between a plurality of positions. It is also to be understood that the number of chamfered edges could be increased or decreased to vary the number of possible positions for the rotatable wing during use e.g., 1, 3, 4, 5, 6, 7, 8, 9, 10, 11, 12 or more locking tabs or chamfered edges.

Figure 17:
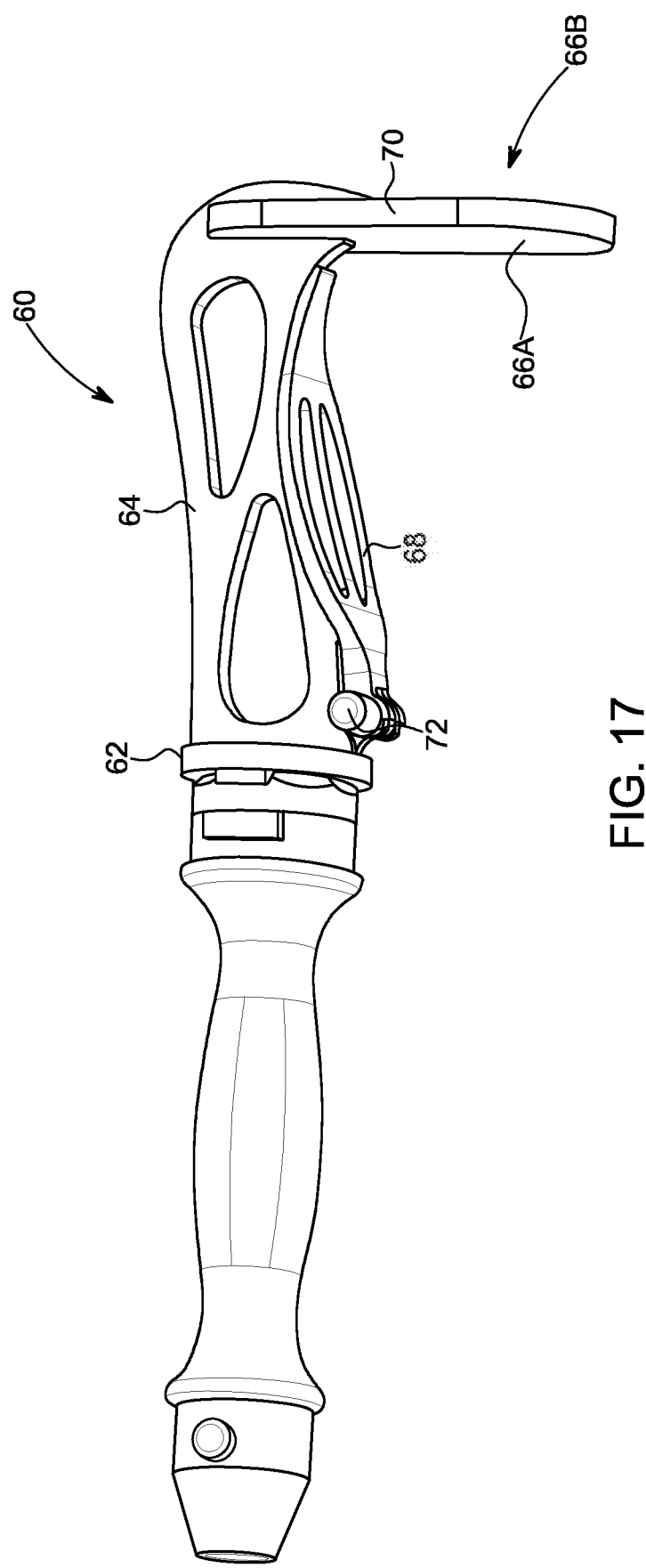
FIG. 17 is a perspective view of a wing assembly in accordance with another exemplary embodiment of the subject disclosure.
Figure 18:
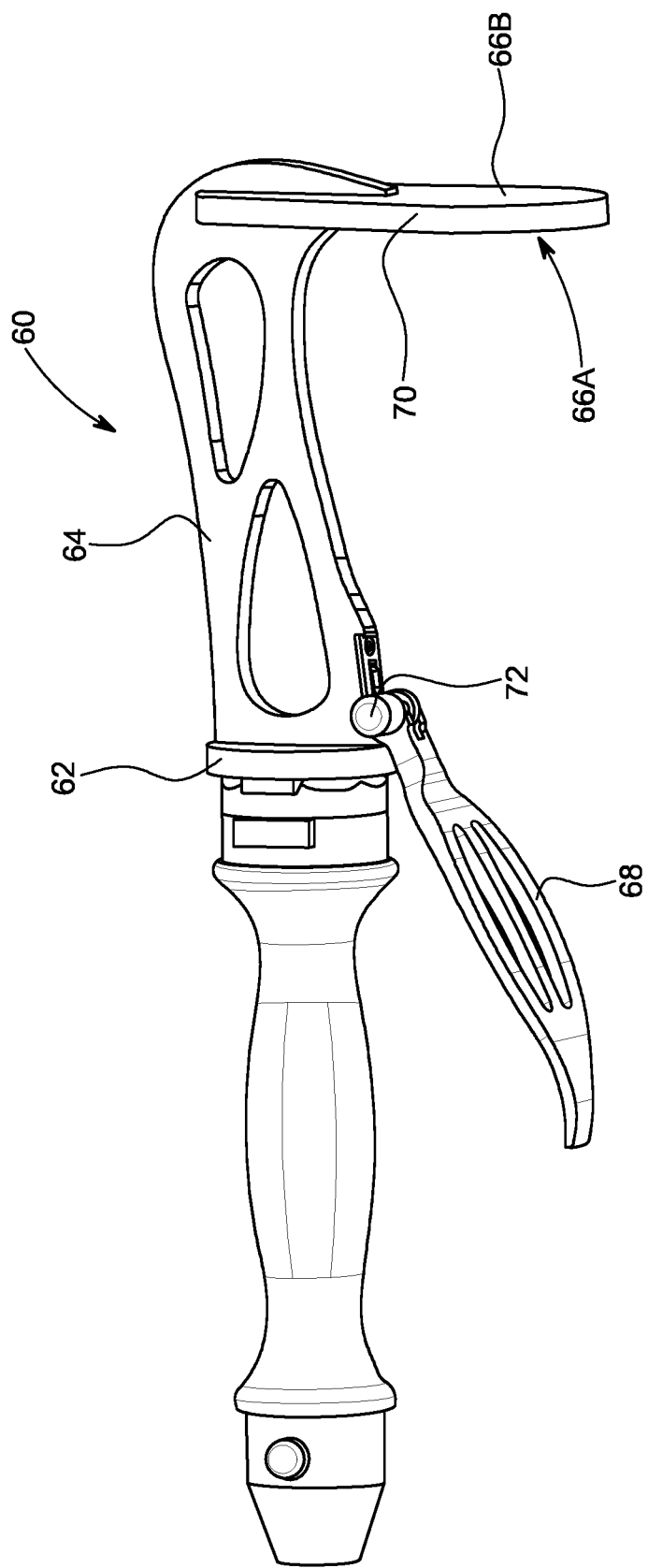
FIG. 18 is another perspective view of the wing assembly of FIG. 17.

In accordance with another exemplary embodiment as shown in FIGS. 17 and 18, the wing can be configured as an extended wing 60. The extended wing 60 includes a base 62 for pivotably mounting the extended wing to the housing, an extension member 64 extending from the base 62, and an impact plate 70 extending radially outwardly from the extension member 64. In an aspect, the extension member 64 extends parallel to a longitudinal axis of the handle 12. Additionally, the impact plate 70 extends radially outwardly from the longitudinal axis of the handle 12. Similar to the wing 20, the extended wing 60 includes a locking mechanism having a detent and preferably a pair of detents extending from the base 62 of the extended wing for selectively engaging the plurality of chamfered edges circumferentially positioned about a periphery of the housing. Accordingly, the extended wing 60 can be releasably secured in a fixed position relative to the longitudinal axis of the handle.

In use, the extended wing 60 facilitates application of an impact force from a surgical tool, such as a hammer. Specifically, the extension member 64 of the extended wing 60 extends a distance between the base 62 and the impact plate 70 to allow additional clearance for a surgical tool, e.g., a hammer, providing an upward or downward force on the impact plate. An impact force can be applied to a bottom surface 66A or a top surface 66B of the impact plate 70 to drive the blade 16 of the osteotome 10 e.g., through bone or cement. The extended wing 60 allows for a hand of a user on the handle 12 to be spaced from the impact plate 70 to avoid interference with any surgical tools during a procedure.

In an aspect, the extended wing 60 further includes a guard 68 pivotably attached to the extension member 64 that is movable between a first position i.e., a retracted position (FIG. 17), and a second position i.e., an extended position (FIG. 18), to provide additional protection to a hand of a user on the handle 12. Specifically, the guard 68 protects the hand of the user from being hit by a surgical tool, e.g., a hammer. As shown in FIGS. 17 and 18, the guard 68 can be adjustably moved between the retracted position and the extended position during a procedure.

In an alternative embodiment, the extended wing 60 can include a locking member 72 to lock or secure the guard 68 in the extended position (FIG. 18). In an aspect, the locking member 72 can be configured as a quick release button. Upon release of the locking member 72, the guard 68 can be biased toward the retracted position (FIG. 17) by a biasing member. In general, the locking member 72 secures the guard 68 in a fixed position.

In sum, the subject disclosure provides an osteotome including a handle, a wing rotatably secured to a proximal end of the handle, and a blade releasably secured to a distal end of the handle. In an aspect, the wing extends substantially perpendicular to a longitudinal axis of the handle.

While the subject disclosure has been described with reference to exemplary embodiments, it will be appreciated by those skilled in the art that various changes may be made and equivalents may be substituted for elements thereof without departing from the scope of the subject disclosure. In addition, modifications may be made to adapt a particular situation or material to the teachings of the exemplary embodiments without departing from the essential scope thereof. It is to be understood, therefore, that the exemplary embodiments not be limited to the particular aspects disclosed, but it is intended to cover modifications within the spirit and scope of the subject disclosure as defined by the appended claims.

I claim:

1. An osteotome comprising:
   a handle;

a blade attachment assembly about a first end of the handle for receiving a blade; and a wing assembly about a second end of the handle opposite the first end, the wing assembly having:
a housing,
a wing extending outwardly from the handle and pivotably mounted to the housing, and
a locking mechanism including a detent extending from the wing and a plurality of corresponding detents about the housing to releasably lock the wing in a fixed position relative to a longitudinal axis of the handle.

2. The osteotome of claim 1, wherein the wing assembly is pivotably mounted to the handle.

3. The osteotome of claim 1, wherein the wing is releasably attached to the housing.

4. The osteotome of claim 1, wherein the housing includes a recess for receiving the wing in the housing.

5. The osteotome of claim 1, wherein the detent is a tab and the plurality of corresponding detents are chamfered edges circumferentially positioned about the housing.

6. The osteotome of claim 1, wherein the wing extends perpendicular to a longitudinal axis of the handle, or wherein the wing is rotatably secured to a proximal end of the handle.

7. The osteotome of claim 1, wherein the blade attachment assembly further comprises:
a housing for receiving a blade, and
a locking mechanism for releasably securing the blade to the housing.

8. The osteotome of claim 7, wherein the housing of the blade attachment assembly includes a recess for receiving the blade, or wherein the locking mechanism includes a pair of detents for engaging a pair of notches on the blade.

9. The osteotome of claim 7, wherein the locking mechanism moves between a locked position and an unlocked position for releasably securing the blade.

10. The osteotome of claim 9, further comprising a biasing member that biases the locking mechanism toward the locked position.

11. The osteotome of claim 1, further comprising a blade releasably secured to the blade attachment assembly.

12. The osteotome of claim 11, wherein the blade includes a pair of notches for aligning the blade with the handle, or wherein the blade includes a plurality of indicators along a length of the blade, or wherein the blade includes a beveled edge.

13. The osteotome of claim 1, wherein the wing comprises:
a base,
an extension member extending from the base, and
an impact plate extending from the extension member.

14. The osteotome of claim 13, wherein the extension member extends parallel to a longitudinal axis of the handle, or wherein the impact plate extends radially outwardly from a longitudinal axis of the handle.

15. The osteotome of claim 13, wherein the wing includes a guard pivotably attached to the extension member.

16. The osteotome of claim 15, wherein the guard is movable between a first position and a second position.

17. The osteotome of claim 15, further comprising a locking member for securing the guard in a fixed position.

18. An osteotome comprising:
a handle;
a blade attachment assembly about a first end of the handle for receiving a blade; and
a wing assembly about a second end of the handle opposite the first end, the wing assembly having:
a housing,
a wing extending outwardly from the handle and pivotably mounted to the housing, the wing including a boss member pivotably attached to the handle, and
a locking mechanism to releasably lock the wing in a fixed position relative to a longitudinal axis of the handle.

19. The osteotome of claim 18, wherein the boss member is concentric with the handle, or wherein the boss member includes a locking groove for securing the wing to a housing.

\* \* \* \* \*